US009895334B2

(12) United States Patent
Ogbourne et al.

(10) Patent No.: US 9,895,334 B2
(45) Date of Patent: Feb. 20, 2018

(54) TREATMENT OF VIRALLY INDUCED LESIONS

(75) Inventors: Steven Martin Ogbourne, Bunya (AU); Andreas Suhrbier, Bunya (AU); James Harrison Aylward, Indooroopilly (AU)

(73) Assignee: LEO Laboratories Limited, Dublin (IE)

( * ) Notice: Subject to any disclaimer, the term of this patent is extended or adjusted under 35 U.S.C. 154(b) by 293 days.

(21) Appl. No.: 12/598,102

(22) PCT Filed: Apr. 30, 2008

(86) PCT No.: PCT/AU2008/000596
§ 371 (c)(1),
(2), (4) Date: Apr. 28, 2010

(87) PCT Pub. No.: WO2008/131491
PCT Pub. Date: Nov. 6, 2008

(65) Prior Publication Data
US 2010/0204318 A1   Aug. 12, 2010

(30) Foreign Application Priority Data
Apr. 30, 2007 (AU) .................. 2007902266

(51) Int. Cl.
| A61K 31/22 | (2006.01) |
| A61K 31/12 | (2006.01) |
| A61K 31/216 | (2006.01) |
| A61K 31/222 | (2006.01) |
| A61K 47/10 | (2017.01) |
| A61K 47/12 | (2006.01) |
| A61K 9/06 | (2006.01) |
| A61K 47/38 | (2006.01) |
| A61K 9/00 | (2006.01) |

(52) U.S. Cl.
CPC .............. *A61K 31/216* (2013.01); *A61K 9/06* (2013.01); *A61K 31/22* (2013.01); *A61K 31/222* (2013.01); *A61K 47/10* (2013.01); *A61K 47/12* (2013.01); *A61K 47/38* (2013.01); *A61K 9/0031* (2013.01); *A61K 9/0034* (2013.01)

(58) Field of Classification Search
CPC .................................................. A61K 31/22
USPC ................................................. 514/549, 690
See application file for complete search history.

(56) References Cited

U.S. PATENT DOCUMENTS 5,804,203 A * 9/1998 Hahn ........................ A61K 8/19
424/401
2003/0195168 A1 10/2003 Aylward et al.
2005/0209192 A1 9/2005 Aylward et al.

FOREIGN PATENT DOCUMENTS

| RU | 2 174 396 | 10/2001 |
| WO | WO 01/93884 | 12/2001 |
| WO | WO 01/93885 | 12/2001 |
| WO | WO 2001/93884 | * 12/2001 |
| WO | WO 2001/93885 | * 12/2001 |
| WO | WO 2006/063382 | 6/2006 |
| WO | WO 2007/053912 | 5/2007 |
| WO | WO 2007/068963 | 6/2007 |

OTHER PUBLICATIONS

Testa "Prodrug Research: Futile or fertile?" Biochemical Pharmacology, 2004, vol. 68, pp. 2097-2106.*
Ogbourne et al. "Antitumor activity of 3-ingenyl angelate: plasma membrane and mitochondrial disruption and necrotic cell death," Cancer Research, 2004, vol. 64, pp. 2833-2839.*
Ogbourne et al., "Proceedings of the First International Conference on PEP005", Anti-Cancer Drugs, vol. 18, No. 3, pp. 357-362 (2007).
Weedon et al., "Home Treatment of Basal Cell Carcinoma", The Medical Journal of Australia, 1: 928 (1976).
Kaminsky et al., "Euphorbia and cantharidine in the topical treatment of verruca", El Dia Medico, Buenos Aires, Jul. 27, 1959; No. 51, Year 31 :1373-80.
International Search Report dated Jul. 23 2008, in corresponding PCT Application No. PCT/AU2008/000596.
Hampson et al., "PEP005, a selective small-molecule activator of protein kinase C, has potent antileukemic activity mediated via the delta isoform of PKC", Blood, 106:4, Aug. 15, 2005, pp. 1362-1368.
Zayed et al., "Dietary cancer risk conditional cancerogens in produce of livestock fed on species of spurge (*Euphorbiaceae*)", J. Cancer Res. Clin Oncol, 124 (1998), pp. 131-140.
Hampson et al., "Treatment of Actinic Keratoses, Acute Myeloid Leukemia Therapy, Treatment of Basal Cell Carcinoma, Protein Kinase C Activator", Drugs of the Future, 30:10, 2005, pp. 1003-1005.
Korotkii , "Modern External Therapy of Dermatoses", External Dermatosis, Moscow 2003, pp. 142-144.
Rohwedder et al., "Epidermodysplasia verruciformis and cutaneous human papillomavirus DNA, but not genital human papillomavirus DNAs, are frequently detected in vulvar and vaginal melanoma", Am J dermatopathol Feb. 2007:29(1):13-7.
Testa, "Prodrug research: futile or fertile?" Biochemical Pharmacology 68 (2004) 2097-2106.
Fujiware et al., "Upregulation of HIV-1 replication in chronically infected cells by ingenol derivatives", Arch Virol (1998) 143: 2003-2010.
Lipke, "An Armamentarium of Wart Treatments", Clinical Medicine & Research, 2006, 4(4), pp. 273-293.

(Continued)

*Primary Examiner* — Shengjun Wang
(74) *Attorney, Agent, or Firm* — Fish & Richardson P.C.

(57) ABSTRACT

The present invention relates generally to the treatment of cutaneous lesions containing cells infected by a virus, as well as compositions for the treatment of such lesions. More specifically, the invention relates to the use of ingenol compounds, particularly ingenol angelates, in treating lesions caused by infection with a papilloma virus, such as a mammalian papilloma virus, in particular a Human Papilloma Virus.

85 Claims, No Drawings

(56) References Cited

OTHER PUBLICATIONS

Katewa et al., "Traditional herbal medicines from Shekhawati region of Rajasthan", Indian Journal of Traditional Knowledge Jul. 2005 4(3) pp. 237-245.
Jain et al., "Traditional uses of some Indian plants among islanders of the Indian Ocean", Indian Journal of traditional Knowledge Oct. 2005 4(4) pp. 345-357.
Jadeja et al., "Indigenous animal healthcare practices in district Porbander, Gujarat", Indian Journal of Traditional Knowledge, Apr. 2006 5(2) pp. 253-258.
Bhatt et al, "Ethnomedicinal plant resources of Jaunsari tribe of Garbwal Himalaya Uttaranchal", Indian Journal of Traditional Knowledge Jul. 2006 5(3) pp. 331-335.
Jeeva et al., "Weeds of Kanyakumari district and their value in rural life", Indian Journal of Traditional Knowledge Oct. 2006 5(4) pp. 501-509.
Jassbi, "Chemistry and biological activity of secondary metabolites in Euphorbia from Iran", *Phytochemistry 2006* 67(18) 1977-1984.
Gibbs et al., "Topical treatments for cutaneous warts (Review)", The Cochrane Library 2012, Issue 10.
Decision on Grant in corresponding Russian Application No. 2009144100/14(062733).
EPO Notice of Opposition to EP Patent No. EP2152261 by Genetics (U.K.) Limited, dated Sep. 9, 2016 (5 pages).
EPO Statement of Facts and Arguments in Notice of Opposition to EP Patent No. EP2152261 by Genetics (U.K.) Limited, dated Sep. 9, 2016 (17 pages).
Clinical Trial extract for NCT00546611, "A Phase I, Single-Centre, Open-Label, Fixed-Dose Study of the Safety and Efficacy of up- to Three-Days Application of 0.05% PEP005 Topical Gel in the Treatment of Patients With Common Wart(s) (*Verruca[e] vulgaris*) on the Dorsal Hand", ClinicalTrials.gov archive, Feb. 14, 2008 (2 pages).
Christensen, "Pointer-Cottontail rabbit papillomavirus (CRPV) model system to test antiviral and immunotherapeutic strategies", Antiviral Chemistry & Chemotherapy 16:355-362 (2005).
Christensen and Kreider, "Animal models of papillomavirus infections", Chapter 125, Handbook of Animal Models of Infection, Academic Press, (1999) pp. 1039-1047.
Drury, S., "Plants and Wart Cures in England from the Seventeenth to the Nineteenth Cenure: Some Examples", Folklore 102(1): 97-100 (1991).
Tanino et al., "Total synthesis of ingenol", J Am Chem Soc., 125(6):1498-500 (Feb. 2003).
Winkler et al., "The First Total Synthesis of (±)-Saudin", J. Am Chem. Soc., 124(33):9726-9728 (Aug. 2002).
EPO Patentee's Response to Opposition for EP Patent No. 2152261 (EP-08733433.3), dated Feb. 24, 2017 (12 pages).
Declaration of Martin Gormsen, M.D., dated Feb. 23, 2017 (27 pages).
Grue-Sorensen et al., *Synthesis, biological evaluation and SAR of 3-benzoates of ingenol for treatment of actinic keratosis and non-melanoma skin cancer*, Bioorganic & Medicinal Chemistry Letters 24:54-60 (2014).
Seborrhoeic Keratoses, British Association of Dermatologists, Patient Information Leaflet, Nov. 2004 (3 pages).
Scheinfeld and Lehman, *An evidence-based review of medical and surgical treatments of genital warts*, Dermatology Online Journal, UC Davis, 12(3):5 (2006) (7 pages).
Epstein and Kligman, *Treatment of Warts with Cantharidine*, Arch. of Dermat. 77(5):508-511 (1958).
Goldblum and Curtis, *Effects of the resin of Euphorbium on verrucae plantares; human and animal experimentation*, J Invest Dermatol. 20(1):45-50 (Jan. 1953).
Marlin-Scott, *Treatment of warts with a varnish containing Euphorbium*, Brit. Jour. of Dermat. 66:57-58 (1954).

\* cited by examiner

TREATMENT OF VIRALLY INDUCED LESIONS

FIELD OF THE INVENTION

The present invention relates generally to the treatment of cutaneous lesions containing cells infected by a virus, as well as compositions for the treatment of such lesions. More specifically, the invention relates to the use of ingenol compounds, particularly ingenol angelates, in treating lesions caused by infection with a papilloma virus, such as a mammalian papilloma virus, in particular a Human Papilloma Virus.

BACKGROUND TO THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Warts are circumscribed cutaneous excrescences or lesions of the skin or mucosa having a papilliferous surface and may be rounded, flat, soft, hard, acuminate or filiform. They are an extremely common occurrence, with most people experiencing them in one form or another at some stage in their lives. They are caused by infection of epithelial cells (cells that form the outer layers of the skin or the lining of body cavities) with a papilloma virus, and in humans, with the Human Papilloma Virus (HPV). Viral replication occurs in fully differentiated epithelium and the ensuing proliferation results in a clinically evident papule or plaque. Any epithelial surface can be affected. Infection is through contact with an infected individual or with an object touched by an infected individual, bathrooms and swimming pools being frequent infective zones. An infected individual may spread warts to uninfected areas of the body through scratching or rubbing existing warts and then touching other areas of skin or mucosa (autoinnoculation). The virus enters the skin or mucous membrane through cuts, abrasions, or other surface disruptions. In the skin the virus replicates primarily in the upper layers of the epidermis in differentiated cells. Following a latency period of several months, and less commonly as much as several years, tiny protuberances appear in the affected area. In the skin, these are hyperkeratotic lesions. The protuberances slowly grow and, in the most common form, result in grayish, rough, rounded structures, though other varieties distinguished by shape and color also occur.

Warts can appear at various sites on the body, most commonly on the skin, genitals and mouth, with their clinical appearance depending to some extent on the type of virus involved and the anatomical site. In humans, common warts (verruca vulgaris) are hyperkeratotic, exophytic and dome-shaped papules or nodules, most commonly located on fingers, hands, knees, elbows or other sites of trauma. Their surface is generally rough and commonly fissured or scaly. Less frequently, they may have a more complex branched or cauliflower-like structure. Two or more papules that are close together sometimes coalesce. Plane or flat warts (also known as juvenile warts; verruca plana juvenilis) are flat topped papules with minimal scaling and only slight elevation (generally about 2-4 mm in diameter). Flat warts are smoother and less elevated than common warts. They tend to be multiple and abundant, sometimes forming large groups of coalescing lesions. Myrmecia are large, deep burrowing warts. They tend to cause more inflammation and pain than other varieties of warts. On the surface they are generally round and dome shaped. They occur mostly on the soles of the feet, the palms, around or under the nails, or less commonly on the face or elsewhere. Myrmecia warts are histologically characterized by an abundance of eosinophilic inclusions. Plantar warts (verruca plantaris) can be painful due to their callused, endophytic papules that have deeply penetrating sloping sides and a central depression. Numerous coalesced warts on the plantar surface will form a tile-like pattern known as mosaic warts. Filiform warts are most often seen on the face with characteristic frond-like projections that exhibit quick proliferation. Periungual warts occur anywhere along the nail margins and can subsequently lead to onychodystrophy from nail matrix damage and onycholysis from nail bed warts. Butcher's warts generally resemble common warts, but with a greater tendency to form complex branched and cauliflower-like structures. They are particularly common around the fingernails. Anogenital warts (venereal or condyloma acuminate) occur in the perineum and on the genitalia or in the genital tract. Warts of the genital tract present a serious health risk to women, being associated with squamous cell- and adeno-carcinomas of the cervix. Oral warts are small pink or white papules in the oral mucosa (M. M. Lipke, *Clinical Medicine & Research*, 2006, 4, 273-293).

Over 80 different types of HPV have been characterized, with several others reported. The most common infections on the hands and feet (verruca vulgaris) are commonly caused by types 1, 2, 3, 4, 7, 26, 27, 29 and 57. Plane or flat warts are distinct from common warts and are generally caused by types 3, 10, 28 or possibly 41. Plantar warts are generally associated with types 1, 2, and 4. Myrmecia warts are caused mainly by type 1, and less commonly by types 2, 3, 4, 27, 29, and 57. Types 6 and 11 are associated with low risk anogenital warts, and types 16, 18, 31, 33, 35, 45, 58, 59 and 66 are commonly associated with squamous cell- and adeno-carcinomas of the cervix.

Warts caused by papilloma virus infection are not limited to humans. Bovine papilloma virus (BPV) is a group of viruses that are highly prevalent in cattle, causing warts of the skin and alimentary tract, as well as teats and udders. Warts caused by BPV-1, 2 and 5 generally have a nodular appearance, with warts caused by BPV-3, 4 and 6 generally having a cauliflower-like appearance, occurring most commonly on the head, neck and shoulders. Although generally harmless, they are unsightly in show animals and large warts may bleed, potentially leading to secondary infections. Florid warts of the teat can cause mastitis and interfere with suckling and milking. Transmission between animals is common, via, for example fences or halters and warts on the teats of lactating cows are readily transmitted to calves via abrasions. Similarly, equine papilloma virus (EPV) cause cauliflower-like growths usually found around the muzzle, lips, nostrils, eyes and occasionally, lower legs, and cross infection occurs readily via fences, halters and feed buckets. Infection by the canine oral papilloma virus (COPV) causes cauliflower-like growths around the lips and muzzle of young animals and on rare occasions, have led to malignancy. Secondary bacterial infections can also occur as a result. Warts arising from papilloma virus infections have been observed for many other animals.

Currently, there is no cure for papilloma virus infection, with therapy aimed at reducing or eliminating symptoms. Non-genital warts in otherwise healthy people or animals are generally harmless and usually resolve spontaneously (within months or years) due to natural immunity. That said, some viral warts persist for many years and may represent a source of further infection. In addition, whilst they are generally harmless, non-genital warts, depending on their location, can be considered cosmetically undesirable, (especially when located on the face or hands) or painful (such as on the soles of the feet and near the nails). Genital warts, however, are sexually transmissible and can, if left untreated, cause cervical cancer in women. In animals, they may interfere with milking, breeding, eating, harnessing and other activities.

Current treatments for warts vary depending on any number of factors, including the size, number and nature of the warts involved, anatomical location, and the health and age of the patient. Treatments include: occlusive duct tape therapy, surgical cutterage or cautery, cryotherapy, chemical therapy, such as topical application of cantharidin, salicylic acid, glutaraldehyde, formaldehyde, formic acid, or silver nitrate, and immunotherapy ((M. M. Lipke, *Clinical Medicine & Research*, 2006, 4, 273-293 and Gibbs, S, and Harvey, I., Topical Treatments for cutaneous warts (Review), *The Cochrane Library*, 2006, Issue 3). However, no one therapy is fully effective in all patients.

SUMMARY OF THE INVENTION

Given the frequent occurrence of warts and their possible health risks or negative cosmetic effects, there remains a need therefore, for new alternative treatments for warts. The present invention is predicated on the discovery that certain ingenol angelate compounds can reduce, retard, resolve, clear or eliminate cutaneous lesions or papules caused by a papilloma virus infection.

In a first aspect, the present invention thus provides a method for treating a cutaneous lesion on a subject, said lesion caused by a virus, comprising administering to said subject an ingenol compound or a pharmaceutically acceptable salt or prodrug thereof.

The virus may be a mammalian papilloma virus. The virus may be HPV or non-HPV. The subject may be human or non-human (for example, a non-human mammal).

In certain embodiments of the invention, the virus is HPV. In further embodiments thereof, the subject is a human subject.

In further embodiments, the virus is selected from those which cause non-genital lesions, including HPV 1, 2, 3, 4, 5, 7, 8, 9 10, 12, 14, 15, 17, 19, 20, 21, 22, 23, 24, 25, 26, 27, 28, 29, 36, 37, 38, 41, 46, 47, 49, 50, 57, 63 and 65.

In other embodiments, the virus is selected from those which cause genital lesions, including HPV 6, 11, 30, 42, 43, 44, 45, 51, 52 and 54.

Examples of lesions contemplated by the invention include: common warts (verruca vulgaris), plane or flat warts, myrmecia, plantar warts, butcher's warts, mosaic warts, filiform warts, periungual warts, anogenital warts (venereal or condyloma acuminate), oral warts, senile warts, digitate warts and palmar warts. In certain further embodiments, the warts are common warts, plantar warts or flat warts.

In other embodiments of the invention, the virus is a non-human mammalian papilloma virus, such as BPV, EPV, CRPV or COPV.

In certain embodiments of the invention, the compound is selected from ingenol-3-angelate, 20-O-acetyl-ingenol-3-angelate and 20-deoxy-ingenol-3-angelate and, pharmaceutically acceptable salts and prodrugs thereof. In a particular example, the compound is ingenol-3-angelate.

In further aspects, the invention also provides ingenol compounds for use in the treatment of cutaneous lesions caused by a virus and the use of ingenol compounds in the manufacture of a medicament therefore, as well as compositions and agents containing ingenol compounds together with a pharmaceutically acceptable carrier.

DETAILED DESCRIPTION OF THE INVENTION

The singular forms "a", "an" and "the" include plural aspects unless the context clearly dictates otherwise. Thus, for example, reference to "an angeloyl substituted ingenane" or "an ingenol angelate" includes a single compound, as well as two or more compounds as appropriate.

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

As used herein, "cutaneous" refers to the epithelial layers of cells of the skin or body cavities. Thus, a cutaneous lesion includes lesions located on the outer skin (epidermis), as well as mucosal linings such as in body cavities (mouth and genital tract) and, perineum and genitalia.

Some particular, but not limiting, embodiments of the present invention contemplate lesions caused by one or more of HPV types 1, 2, 3, 4, 5, 6, 7, 8, 9, 10, 11, 12, 14, 15, 17, 19, 20, 21, 22, 23, 24, 25, 26, 27, 28, 29, 30, 36, 37, 38, 41, 42, 43, 44, 45, 46, 47, 49, 50, 51, 52, 54, 57, 63 and 65.

Lesions caused by non-human papilloma viruses, e.g. canine, bovine, equine, feline, deer, rabbit and avian papilloma viruses are contemplated by other embodiments of the invention.

Examples of cutaneous lesions and their commonly associated HPV types contemplated by the present invention are presented below in Table 1, although it will be understood that one virus type may be responsible for different types of lesions or warts, and more than one HPV type may be responsible for a type of lesion or wart.

TABLE 1

Lesions and commonly Associated HPV Subtypes

| | HPV Type |
|---|---|
| Nongenital Cutaneous Disease | |
| Common warts (verrucae vulgaris) | 1, 2, 4, 7, 26, 27, 29, 41, 57, 65 |
| Plantar warts (myrmecias) | 1, 2, 4, 63 |
| Flat warts (verrucae plana) | 3, 10, 27, 28, 38, 41, 49 |
| Butcher's warts | 1, 2, 3, 4, 7, 10, 28 |
| Mosaic warts | 2, 27, 57 |
| Epidermodysplasia verruciformis (benign) | 2, 3, 10, 12, 15, 19, 36, 46, 47, 50 |
| Epidermodysplasia Verruciformis | |
| Epidermodysplasia verruciformis (malignant or benign) | 5, 8, 9, 10, 14, 17, 20, 21, 22, 23, 24, 25, 37, 38 |
| Epidermodysplasia Verruciformis | |
| Nonwarty skin lesions | 37, 38 |
| Nongenital Mucosal Disease | |
| Respiratory papillomatosis | 6, 11 |
| Recurrent Respiratory Papillomatosis | |
| Laryngeal papilloma | 6, 11, 30 |
| Maxillary sinus papilloma | 57 |
| Conjunctival papillomas | 6, 11 |

TABLE 1-continued

Lesions and commonly Associated HPV Subtypes

| | HPV Type |
|---|---|
| Anogenital Disease | |
| Condylomata acuminata | 6, 11, 30, 42, 43, 44, 45, 51, 52, 54 |
| Giant condylomata (Buschke-Lowenstein tumors) | 6, 11 |
| Giant Condylomata Acuminata of Buschke and Lowenstein | |

Particular examples of lesions caused by HPV contemplated by the present invention are non-cancerous and include: common warts (verruca vulgaris), plane or flat warts, myrmecia, plantar warts, butcher's warts (commonly associated with those who regularly handle raw meat, fish or poultry) mosaic warts, filiform warts, periungual warts, anogenital warts (venereal or condyloma acuminate), oral warts, senile warts, digitate warts and palmar warts. In certain further embodiments, the warts are common warts.

In humans, in some embodiments, the lesion may be located on any part of the body, other than the anogenital region, for example, the face, hands, feet, elbows or knees. In other embodiments, the lesion may be located on the anogenital region, e.g. penis, vulva or anus. In animals, the lesion may be located on the head (e.g. muzzle, mouth, nose, lips), body (e.g. legs, back, neck, shoulders) or the anogenital area.

Reference to an "ingenol" includes compounds having the C3, C4, C5-trioxy trans bicyclo[4.4.1]-undecane ingenane skeleton. Such compounds are extensively reported and known in the literature and can be isolated from plants such as from a species of the family Euphorbiaceae or fully or partially chemically synthesized (see for example Winkler et al, *J. Am. Chem. Soc.*, 2002, 124, 9726 and Tanino et al, *J. Am. Chem. Soc.*, 2003, 125, 1498-1500). Synthetically prepared ingenol compounds may include stereoisomers of naturally occurring ingenols. Thus racemates and stereoisomeric mixtures are also contemplated herein. The compounds are generally found in extracts of the Euphorbiaceae plants. An extract may comprise, therefore, sap or liquid or semi-liquid material exuded from, or present in, leaves, stem, flowers, seeds, bark or between the bark and the stem. Most preferably, the extract is from sap. Furthermore, the extract may comprise liquid or semi-liquid material located in fractions extracted from sap, leaves, stems, flowers, bark or other plant material of the Euphorbiaceae plant. For example, plant material may be subject to physical manipulation to disrupt plant fibres and extracellular matrix material and inter- and intra-tissue extracted into a solvent including an aqueous environment. All such sources of the compounds are encompassed by the present invention including compounds obtained by chemically synthetic routes.

Reference herein to a member of the Euphorbiaceae family includes reference to species from the genera *Acalypha, Acidoton, Actinostemon, Adelia, Adenocline, Adenocrepis, Adenophaedra, Adisca, Agrostistachys, Alchornea, Alchorneopsis, Alcinaeanthus, Alcoceria, Aleurites, Amanoa, Andrachne, Angostyles, Anisophyllum, Antidesma, Aphora, Aporosa, Aporosella, Argythamnia, Astrococcus, Astrogyne, Baccanrea, Baliospermum, Bernardia, Beyeriopsis, Bischofia, Blachia, Blumeodondron, Bonania, Bradleia, Breynia, Breyniopsis, Briedelia, Buraeavia, Caperonia, Caryodendron, Celianella, Cephalocroton, Chaenotheca, Chaetocarpus, Chamaesyce, Cheilosa, Chiropetalum, Choriophyllum, Cicca, Chaoxylon, Cleidon, Cleistanthus, Cluytia, Cnesmone, Cnidoscolus, Coccoceras, Codiaeum, Coelodiscus, Conami, Conceveiba, Conceveibastrum, Conceveïbum, Corythea, Croizatia, Croton, Crotonopsis, Crozophora, Cubanthus, Cunuria, Dactylostemon, Dalechampia, Dendrocousinsia, Diaspersus, Didymocistus, Dimorphocalyx, Discocarpus, Ditaxis, Dodecastingma, Drypetes, Dysopsis, Elateriospermum, Endadenium, Endospermum, Erismanthus, Erythrocarpus, Erythrochilus, Eumecanthus, Euphorbia, Euphorbiodendron, Excoecaria, Flueggea, Calearia, Garcia, Gavarretia, Gelonium, Giara, Givotia, Glochidion, Clochidionopsis, Glycydendron, Gymnanthes, Gymnosparia, Haematospermum, Hendecandra, Hevea, Hieronima, Hieronyma, Hippocrepandra, Homalanthus, Hymenocardia, Janipha, Jatropha, Julocroton, Lasiocroton, Leiocarpus, Leonardia, Lepidanthus, Leucocroton, Mabea, Macaranga, Mallotus, Manihot, Mappa, Maprounea, Melanthesa, Mercurialis, Mettenia, Micrandra, Microdesmis, Microelus, Microstachy, Maocroton, Monadenium, Mozinna, Neoscortechinia, Omalanthus, Omphalea, Ophellantha, Orbicularia, Ostodes, Oxydectes, Palenga, Pantadenia, Paradrypeptes, Pausandra, Pedilanthus, Pera, Peridium, Petalostigma, Phyllanthus, Picrodendro, Pierardia, Pilinophytum, Pimeleodendron, Piranhea, Platygyna, Plukenetia, Podocalyx, Poinsettia, Poraresia, Prosartema, Pseudanthus, Pycnocoma, Quadrasia, Reverchonia, Richeria, Richeriella, Ricinella, Ricinocarpus, Rottlera, Sagotia, Sanwithia, Sapium, Savia, Sclerocroton, Sebastiana, Securinega, Senefeldera, Senefilderopsis, Serophyton, Siphonia, Spathiostemon, Spixia, Stillingia, Strophioblachia, Synadenium, Tetracoccus, Tetraplandra, Tetrorchidium, Thyrsanthera, Tithymalus, Trageia, Trewia, Trigonostemon, Tyria* and *Xylophylla*.

A preferred genus and particularly suitable for the practice of the present invention is the genus *Euphorbia*. Particularly useful species of this genus include *Euphorbia aaronrossii, Euphorbia abbreviate, Euphorbia acuta, Euphorbia alatocaulis, Euphorbia albicaulis, Euphorbia algomarginata, Euphorbia aliceae, Euphorbia alta, Euphorbia anacampseros, Euphorbia andromedae, Euphorbia angusta, Euphorbia anthonyi, Euphorbia antiguensis, Euphorbia apocynifolia, Euphorbia arabica, Euphorbia ariensis, Euphorbia arizonica, Euphorbia arkansana, Euphorbia arteagae, Euphorbia arundelana, Euphorbia astroites, Euphorbia atrococca, Euphorbia baselicis, Euphorbia batabanensis, Euphorbia bergeri, Euphorbia bermudiana, Euphorbia bicolor, Euphorbia biformis, Euphorbia bifurcata, Euphorbia bilobata, Euphorbia biramensis, Euphorbia biuncialis, Euphorbia blepharostipula, Euphorbia blodgetti, Euphorbia boerhaavioides, Euphorbia boliviana, Euphorbia bracei, Euphorbia brachiate, Euphorbia brachycera, Euphorbia brandegee, Euphorbia brittonii, Euphorbia caesia, Euphorbia calcicola, Euphorbia campestris, Euphorbia candelabrum, Euphorbia capitellata, Euphorbia carmenensis, Euphorbia carunculata, Euphorbia cayensis, Euphorbia celastroides, Euphorbia chalicophila, Euphorbia chamaerrhodos, Euphorbia chamaesula, Euphorbia chiapensis, Euphorbia chiogenoides, Euphorbia cinerascens, Euphorbia clarionensis, Euphorbia colimae, Euphorbia colorata, Euphorbia commutata, Euphorbia consoquitlae, Euphorbia convolvuloides, Euphorbia corallifera, Euphorbia creberrima, Euphorbia crenulata, Euphorbia cubensis, Euphorbia cuspidata, Euphorbia cymbiformis, Euphorbia darlingtonii, Euphorbia defoliata, Euphorbia degeneri, Euphorbia deltoidea, Euphorbia dentata, Euphorbia depressa Euphorbia dictyosperma, Euphorbia dictyosperma, Euphorbia dioeca, Euphorbia discoidalis, Euphorbia dorsiventralis, Euphor-* bia drumondii, Euphorbia duclouxii, Euphorbia dussii, Euphorbia eanophylla, Euphorbia eggersii, Euphorbia eglandulosa, Euphorbia elata, Euphorbia enalla, Euphorbia eriogonoides, Euphorbia eriophylla, Euphorbia esculaeformis, Euphorbia espirituensis, Euphorbia esula, Euphorbia excisa, Euphorbia exclusa, Euphorbia exstipitata, Euphorbia exstipulata, Euphorbia fendleri, Euphorbia filicaulis, Euphorbia filiformis, Euphorbia florida, Euphorbia fruticulosa, Euphorbia garber, Euphorbia gaumerii, Euphorbia gerardiana, Euphorbia geyeri, Euphorbia glyptosperma, Euphorbia gorgonis, Euphorbia gracilior, Euphorbia gracillima, Euphorbia gradyi, Euphorbia graminea, Euphorbia graminiea Euphorbia grisea, Euphorbia guadalajarana, Euphorbia guanarensis, Euphorbia gymnadenia, Euphorbia haematantha, Euphorbia hedyotoides, Euphorbia heldrichii, Euphorbia helenae, Euphorbia helleri, Euphorbia helwigii, Euphorbia henricksonii, Euphorbia heterophylla, Euphorbia hexagona, Euphorbia hexagonoides, Euphorbia hinkleyorum, Euphorbia hintonii, Euphorbia hirtula, Euphorbia hirta, Euphorbia hooveri, Euphorbia humistrata, Euphorbia hypericifolia, Euphorbia inundata, Euphorbia involuta, Euphorbia jaliscensis, Euphorbia jejuna, Euphorbia johnston, Euphorbia juttae, Euphorbia knuthii, Euphorbia lasiocarpa, Euphorbia lata, Euphorbia latazi, Euphorbia latericolor, Euphorbia laxiflora Euphorbia lecheoides, Euphorbia ledienii, Euphorbia leucophylla, Euphorbia lineata, Euphorbia linguiformis, Euphorbia longecornuta, Euphorbia longepetiolata, Euphorbia longeramosa, Euphorbia longinsulicola, Euphorbia longipila, Euphorbia lupulina, Euphorbia lurida, Euphorbia lycioides, Euphorbia macropodoides, macvaughiana, Euphorbia manca, Euphorbia mandoniana, Euphorbia mangleti, Euphorbia mango, Euphorbia marylandica, Euphorbia mayana, Euphorbia melanadenia, Euphorbia melanocarpa, Euphorbia meridensis, Euphorbia mertonii, Euphorbia mexiae, Euphorbia microcephala, Euphorbia microclada, Euphorbia micromera, Euphorbia misella, Euphorbia missurica, Euphorbia montana, Euphorbia montereyana, Euphorbia multicaulis, Euphorbia multiformis, Euphorbia multinodis, Euphorbia multiseta, Euphorbia muscicola, Euphorbia neomexicana, Euphorbia nephradenia, Euphorbia niqueroana, Euphorbia oaxacana, Euphorbia occidentalis, Euphorbia odontodenia, Euphorbia olivacea, Euphorbia olowaluana, Euphorbia opthalmica, Euphorbia ovata, Euphorbia pachypoda, Euphorbia pachyrhiza, Euphorbia padifolia, Euphorbia palmeri, Euphorbia paludicola, Euphorbia parciflora, Euphorbia parishii, Euphorbia parryi, Euphorbia paxiana, Euphorbia pediculifera, Euphorbia peplidion, Euphorbia peploides, Euphorbia peplus, Euphorbia pergamena, Euphorbia perlignea, Euphorbia petaloidea, Euphorbia petaloidea, Euphorbia petrina, Euphorbia picachensis, Euphorbia pilosula, Euphorbia pilulifera, Euphorbia pinariona, Euphorbia pinetorum, Euphorbia pionosperma, Euphorbia platysperma, Euphorbia plicata, Euphorbia poeppigii, Euphorbia poliosperma, Euphorbia polycarpa, Euphorbia polycnemoides, Euphorbia polyphylla, Euphorbia portoricensis, Euphorbia portulacoides Euphorbia portulana, Euphorbia preslii, Euphorbia prostrata, Euphorbia pteroneura, Euphorbia pycnanthema, Euphorbia ramosa, Euphorbia rapulum, Euphorbia remyi, Euphorbia retroscabra, Euphorbia revoluta, Euphorbia rivularis, Euphorbia robusta, Euphorbia romosa, Euphorbia rubida, Euphorbia rubrosperma, Euphorbia rupicola, Euphorbia sanmartensis, Euphorbia saxatilis M. Bieb, Euphorbia schizoloba, Euphorbia sclerocyathium, Euphorbia scopulorum, Euphorbia senilis, Euphorbia serpyllifolia, Euphorbia serrula, Euphorbia setiloba Engelm, Euphorbia sonorae, Euphorbia soobyi, Euphorbia sparsiflora, Euphorbia sphaerosperma, Euphorbia syphilitica, Euphorbia spruceana, Euphorbia subcoerulea, Euphorbia stellata, Euphorbia submammilaris, Euphorbia subpeltata, Euphorbia subpubens, Euphorbia subreniforme, Euphorbia subtrifoliata, Euphorbia succedanea, Euphorbia tamaulipasana, Euphorbia telephioides, Euphorbia tenuissima, Euphorbia tetrapora, Euphorbia tirucalli, Euphorbia tomentella, Euphorbia tomentosa, Euphorbia torralbasii, Euphorbia tovariensis, Euphorbia trachysperma, Euphorbia tricolor, Euphorbia troyana, Euphorbia tuerckheimii, Euphorbia turczaminowii, Euphorbia umbellulata, Euphorbia undulata, Euphorbia vermiformis, Euphorbia versicolor, Euphorbia villifera, Euphorbia violacea, Euphorbia whitei, Euphorbia xanti Engelm, Euphorbia xylopoda Greenm, Euphorbia yayalesia Urb., Euphorbia yungasensis, Euphorbia zerayschanica and Euphorbia zinniiflora.

Particularly preferred species of the genus *Synadenium* include *Synadenium grantii* and *Synadenium compactum*.

Particularly preferred species of the genus *Monadenium* include *Monadenium lugardae* and *Monadenium guentheri*.

A preferred species of the genus *Endadenium* is *Endadenium gossweileni*.

*Euphorbia peplus* is particularly useful in the practice of the present invention in terms of providing a source of ingenol angelates. Reference herein to "*Euphorbia peplus*" or its abbreviation "*E. peplus*" includes various varieties, strains, lines, hybrids or derivatives of this plant as well as its botanical or horticultural relatives. Furthermore, the present invention may be practiced using a whole Euphorbiaceae plant or parts thereof including sap or seeds or other reproductive material may be used. Generally, for seeds or reproductive material to be used, a plant or plantlet is first required to be propagated.

Reference herein to a Euphorbiaceae plant, a *Euphorbia* species or *E. peplus* further encompasses genetically modified plants. Genetically modified plants include transgenic plants or plants in which a trait has been removed or where an endogenous gene sequence has been down-regulated, mutated or otherwise altered including the alteration or introduction of genetic material which exhibits a regulatory effect on a particular gene. Consequently, a plant which exhibits a character not naturally present in a Euphorbiaceae plant or a species of *Euphorbia* or in *E. peplus* is nevertheless contemplated by the present invention and is included within the scope of the above-mentioned terms.

In one embodiment of the invention, the ingenol compound has the formula:

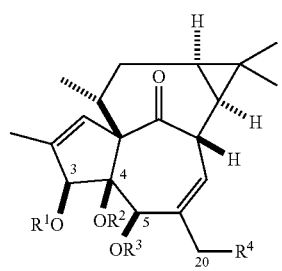

wherein
R$^1$-R$^3$ are independently selected from hydrogen, optionally substituted alkyl, optionally substituted alkenyl, optionally substituted alkynyl, optionally substituted acyl, optionally substituted aryl, optionally substituted arylalkyl, S(O)$_2$R', S(O)$_2$OR', P(O)(OR')$_2$ (wherein R' is hydrogen, alkyl, alkenyl, alkynyl, acyl, aryl, or arylalkyl) and glycosyl; and R$^4$ is selected from hydrogen, hydroxy, optionally substituted alkoxy, optionally substituted alkenoxy, optionally substituted alkynoxy, optionally substituted acyloxy, optionally substituted arylalkoxy, OS(O)$_2$R', OS(O)$_2$OR', OP(O)(OR')$_2$ (wherein R' is hydrogen, alkyl, alkenyl, alkynyl, acyl, aryl, or arylalkyl) and glycoxy.

In one embodiment of the invention, at least one of R$^1$-R$^4$ is not hydrogen. In a particular example thereof, R$^1$ is not hydrogen.

In one particular embodiment of the invention, R$^1$ is an optionally substituted acyl group C(O)—R. In further embodiments thereof, R is optionally substituted alkyl, alkenyl or alkynyl. In a more preferred embodiment thereof, R may be straight chain or branched and may have up to 6 or up to 10 carbon atoms. In one embodiment thereof, R is branched.

In certain embodiments of the invention, one of R$^1$-R$^3$ is an angeloyl group, as depicted by the formula below, or R$^4$ is an O-angeloyl group. Such compounds are referred to herein as ingenol angelates. In a particularly preferred embodiment of the invention, R$^1$ is an angeloyl group.

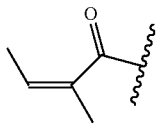 [SMILES: *C(=O)/C(C)=C\C]

In certain embodiments of the invention one or both of R$^2$ and R$^3$ are hydrogen. R$^2$ and R$^3$ may also form a methylene or ethylene dioxy group.

In certain embodiments of the invention R$^4$ is hydrogen, hydroxy or acyloxy, such as acetoxy.

In certain embodiments of the invention, compounds for use in the described methods are ingenol-3-angelate, 20-O-acetyl-ingenol-3-angelate and 20-deoxy-ingenol-3-angelate (depicted below) and pharmaceutically acceptable salts and prodrugs thereof.

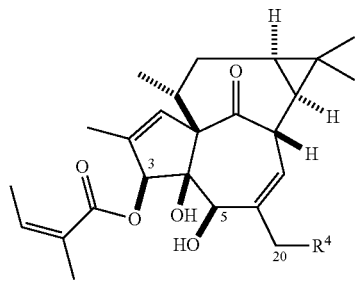

R$^4$ = OH, ingenol-3-angelate
R$^4$ = OAc, 20-O-Acetyl-ingenol-3-angelate
R$^4$ = H, 20-deoxy-ingenol-3-angelate In a particular embodiment of the present invention the compound is ingenol-3-angelate. Reference herein to "ingenol-3-angelate" includes naturally occurring as well as chemically synthetic forms.

Alkylation, alkenylation, alkynylation, arylation, arylalkylation or acylation can be carried out on the ingenol compounds using methods known in the art of synthetic chemistry for alkylating, alkenylation, alkynylation, arylation, arylalkylating or acylating free hydroxy groups (see for example, Greene and Wutz, Protective Groups in Organic Synthesis, 1999; March, *Advanced Organic Chemistry*, 5$^{th}$ Edition; Larock, Comprehensive Organic Transformations, 1999; the entire contents of which are incorporated herein by reference). For example, hydroxy groups can be alkylated (or arylalkylated) using alkyl (or arylalkyl) halides, such as methyl iodide (or benzylbromide), or dialkyl sulfates, such as dimethyl or diethyl sulfate. Acylation can be effected by treatment with appropriate carboxylic acids, acid halides and acid anhydrides in the presence of a base or a coupling agent. Glycosidic formation may be effected chemically, for example, by reacting the ingenol compound with a protected sugar compound in which C-1 has been activated by halogenation for coupling with the hydroxyl or carboxyl groups and the sugar hydroxyl groups have been blocked by protecting groups. Alternatively, glycoside formation may be effected enzymatically using an appropriate glycosyltransferase such as UDP-galactose dependent galactocyltransferase and UDP-glucose dependent glycotransferase. Preferred C-1 linked saccharides area furanose or pyranose saccharide (sugar) substituent which is linked to the ingenol angelate structure through C-1 of the saccharide (conventional numbering) to form an acetyl linkage. Exemplary saccharide groups include reducing sugars such as glucose, ribose, arabinose, xylose, mannose and galactoses, each being linked to an oxygen atom of the ingenol compound.

Sulfate, sulfonate and phosphate groups can be prepared by method known in the art. Examples of R' include hydrogen, C$_{1-6}$alkyl, phenyl and benzyl.

As used herein, the term "alkyl" denotes straight chain, or branched alkyl, preferably C$_{1-20}$ alkyl, e.g. C$_{1-10}$ or C$_{1-6}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Where an alkyl group is referred to generally as "propyl", "butyl" etc, it will be understood that this can refer to any of straight, branched and cyclic isomers where appropriate. An alkyl group may be optionally substituted by one or more optional substituents as herein defined. A "cycloalkyl" group is a cyclic alkyl group of at least 3 carbon atoms, e.g. C$_3$-C$_8$, such as C$_3$, C$_4$, C$_5$ or C$_6$ cycloalkyl. Examples of "cycloalkyl" include mono- or polycyclic alkyl groups such as cyclopropyl, cyclobutyl, cyclopentyl, cyclohexyl, cycloheptyl, cyclooctyl, cyclononyl, cyclodecyl and the like. A cycloalkyl group may be optionally substituted by one or more optional substituents as herein defined.

The term "alkenyl" as used herein denotes groups formed from straight chain, branched or cyclic hydrocarbon residues containing at least one carbon to carbon double bond including ethylenically mono-, di- or poly-unsaturated alkyl or cycloalkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethynically mono-, di- or poly-unsaturated alkyl or cycloalkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substitutents as herein defined.

The term "aryl" denotes any of single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may be optionally substituted by one or more optional substituents as herein defined.

The term "acyl" denotes a group C(O)—R, wherein R can be a hydrogen, alkyl, cycloalkyl, alkenyl, alkynyl, arylalkyl or aryl residue. Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; straight chain or branched alkenoyl (e.g. $C_{2-20}$) such as angeloyl; and aroyl such as benzoyl, toluoyl and naphthoyl. The R residue may be optionally substituted as described herein.

An arylalkyl group is an alkyl group as defined herein, substituted by an aryl group as defined herein. In one embodiment, the alkyl group is terminally substituted by the aryl group. Examples of arylalkyl include phenyl$C_1$-$C_{20}$alkyl such as benzyl, phenylethyl, phenylpropyl, phenylbutyl, phenylpentyl and phenylhexyl. One or both of the alkyl and aryl groups may be independently optionally substituted by one or more optional substituents as described herein.

The term "optionally substituted" means that a group may be unsubstituted or substituted by one or more, same or different, substituents. Optional substituents for alkyl, alkenyl, alkynyl, aryl, arylalkyl, aryl, and thus acyl, include: halo(chloro, bromo, iodo and fluoro), hydroxy, $C_{1-6}$ alkoxy, $C_{1-6}$alkyl, $C_{3-6}$cycloalkyl, phenyl, nitro, halomethyl (e.g. tribromomethyl, trichloromethyl, trifluoromethyl), halomethoxy (e.g. trifluoromethoxy, tribromomethoxy), $C(O)C_{1-6}$alkyl, amino($NH_2$), $C_{1-6}$alkylamino, (e.g. methylamino, ethylamino and propylamino) di$C_{1-6}$alkylamino (e.g. dimethylamino, diethylamino and dipropylamino), $CO_2H$, $CO_2C_{1-6}$ alkyl, thio (SH) and $C_{1-6}$alkylthio. An optional substituent also includes the replacement of a $CH_2$ group by a carbonyl(C═O) group or may be a methylene or ethylene dioxy group.

It will be recognized that during synthetic or semisynthetic processes for the preparation of ingenol compounds contemplated by the present invention, it may be necessary or desirable to protect other functional groups which may be reactive or sensitive to the reaction or transformation conditions undertaken. Suitable protecting groups for such functional groups are known in the art and may be used in accordance with standard practice. As used herein, the term "protecting group", refers to an introduced functionality which temporarily renders a particular functional group inactive. Such protecting groups and methods for their installation and subsequent removal at an appropriate stage are well known (Greene and Wutz, 1999 supra).

The present invention also relates to prodrugs of ingenol compounds. Any compound that is a prodrug of an ingenol compound is within the scope and spirit of the invention. The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as an acetate, or thioester or where a free amino group is converted into an amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters $C_{1-6}$alkyl esters; $C_{1-6}$alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, *Adv. BioSci.*, 1979, 20, 369, Kyncl, J. et al), enamines (see, for example, *J. Pharm. Sci.*, 1971, 60, 1810, Caldwell, H. et al), Schiff bases (see, for example, U.S. Pat. No. 2,923,661 and *Antimicrob. Agents Chemother.*, 1981, 19, 1004, Smyth, R. et al), oxazolidines (see, for example, *J. Pharm. Sci*, 1983, 72, 1294, Johansen, M. et al), Mannich bases (see, for example, *J. Pharm. Sci.* 1980, 69, 44, Bundgaard, H. et al and *J. Am. Chem. Soc.*, 1959, 81, 1198, Gottstein, W. et al), hydroxymethyl derivatives (see, for example, *J. Pharm. Sci*, 1981, 70, 855, Bansal, P. et al) and N-(acyloxy)alkyl derivatives and carbamates (see, for example, *J. Med. Chem.*, 1980, 23, 469, Bodor, N. et al, *J. Med. Chem.*, 1984, 27, 1037, Firestone, R. et al, *J. Med. Chem.*, 1967, 10, 960, Kreiger, M. et al, U.S. Pat. No. 5,684,018 and *J. Med. Chem.*, 1988, 31, 318-322, Alexander, J. et al). Other conventional procedures for the selection and preparation of suitable prodrugs are known in the art and are described, for example, in WO 00/23419;

Design of Prodrugs, H. Bundgaard, Ed., Elsevier Science Publishers, 1985; Methods in Enzymology, 42: 309-396, K. Widder, Ed, Academic Press, 1985; A Textbook of Drug Design and Development, Krogsgaard-Larsen and H. Bundgaard, Eds, Chapter 5, p 113-191 (1991); Advanced Drug Delivery Reviews, 8; 1-38 (1992); Journal of Pharmaceutical Sciences, 77; 285 (1988), H. Bundgaard, et al; Chem Pharm Bull, 32692 (1984), N. Kakeya et al and The Organic Chemistry of Drug Desig and Drug Action, Chapter 8, pp 352-401, Academic press, Inc., 1992.

Suitable pharmaceutically acceptable salts of compounds include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicyclic sulphanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The compounds of the invention may be in crystalline form either as the free compounds or as solvates (for example, of water, i.e. hydrates, or of common organic solvents such as alcohols) and it is intended that both forms are within the scope of the present invention. Methods of solvation are generally known within the art, for example recrystallisation from a given solvent.

As used herein the word "treating" or "treatment" refers to the regression, elimination, partial or full removal or detachment, clearance, reduction in size (e.g. surface area or volume), or otherwise desired decrease in size, number or growth rate of the lesion(s).

Thus, in one or more embodiments of the invention, the use of ingenol compounds in treating lesions (warts) may advantageously promote or improve the rate, degree, extent or time taken for elimination, removal, clearance, reduction in size, or otherwise decrease in size, growth rate or number of lesions on the patient. In further embodiments, the warts may regress or may be eliminated without scarring or, pigmentation changes. In further embodiments, once a lesion is treated and eliminated, subsequent re-infection by the lesion causing virus(es) may not result in the formation of new lesions. In other embodiments, it may only be necessary to treat one or some of a number of lesions to achieve a desired overall therapeutic effect such as elimination of all lesions. A reduction in the size or growth rate of the lesions can be quantitatively determined by measuring the surface area of the lesion. The surface area may be determined according to the formula: Length×Width×π.

Whilst the lesions to be treated may be of any size (surface area), for example, having a surface area greater than about 500 or even 1000 $mm^2$, in certain embodiments of the invention, the lesion(s) to be treated advantageously have a surface area of about 250 $mm^2$ or less. In further embodiments thereof the lesion(s) have a surface area of about 150 or 100 $mm^2$ or less. In still further embodiments, the lesion(s) have a surface area of about 75 or 50, 25 or 10 $mm^2$ or less.

The virus causing the lesions on a subject may be a human or non-human papilloma virus.

Thus, subjects which may be treated in accordance with the present invention include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention. A subject may also be referred to herein as an individual, patient, animal or recipient. Subjects may be afflicted with a papilloma virus originating from a different species, e.g. inter species transmission has been documented for bovine papilloma virus.

The ingenol compounds are administered to the subject in therapeutically or treatment effective amounts. Suitable effective amounts for administration (dosage) and dosing regimens can be determined by the attending physician and may depend on the particular anatomical site or nature, size or number of the lesion(s) being treated, as well as the general age, and health of the subject.

While it is possible for the ingenol compound active ingredient to be administered alone, it is preferable to present it as a composition, preferably as a pharmaceutical composition, with one or more pharmaceutically acceptable adjuvants. Thus, the present invention also relates to the use of an ingenol compound or a pharmaceutically acceptable salt, or prodrug thereof in the manufacture of a medicament for treating a cutaneous lesion caused by HPV.

Medicaments or compositions suitable for use in the invention may contain the ingenol angelate compound in an amount of from about 0.0001% to up to 100% by weight. In preferred embodiments, the composition contains the ingenol compound in an amount of from about 0.0001% to up to about 10% by weight, for example about 0.0005, 0.001, 0.0025, 0.005, 0.01, 0.025, 0.05, 0.075, 0.1, 0.125, 0.15, 0.2, 0.25 or 0.5% to about 0.5, 1.0, 2.5 or 5.0%. In one embodiment of the invention, the ingenol compound is ingenol-3-angelate present in an amount of about 0.001 to about 1%. In a further embodiment the ingenol compound, for example ingenol-3-angelate is present in an amount of about 0.01 to about 0.2%. In a further embodiment thereof, the ingenol compound, such as ingenol-3-angelate, may be present in an amount of from 0.05 to 0.15%, such as about 0.1%.

The ingenol compounds may be administered in any suitable form, such as locally, e.g. by topical application to, and/or the area surrounding, the lesion or by injection into the lesion. In particular examples of the invention, the ingenol compound is administered by topical application to the lesion.

The method of delivery of the active agent may vary, but necessarily involves application of a formulation of the invention to and/or in proximity to an area of body surface affected with one or more lesions. For example, a suitable formulation such as cream, aqueous gel, ointment, paste, plaster, or lotion may be spread on, and/or around the base of, the lesion or lesions and optionally, gently rubbed in. Similarly, a polymeric or other bioadhesive formulation may be spread or dabbed on the lesions. In another embodiment, the active agent may be delivered as a spray formulation, for example an aerosol or atomised spray. A solution may be applied in the same ways, but more typically will be applied with a dropper, swab, or the like, and carefully applied to and/or around the lesions. Alternatively, the ingenol compound may be impregnated into or coated onto an occlusive dressing which is then placed over the affected area. Petrolatum may be spread on the skin surrounding the lesion to protect it from possible irritation during treatment. Where more than one lesion exists, it may only be necessary to administer the ingenol compound to one or some, rather than all, of the lesions.

The dose regimen will depend on a number of factors that may readily be determined, such as the size of the lesion(s) and/or number of lesions and the responsiveness of the lesions to treatment, but will normally be one or more doses per day, with a course of treatment lasting from several days to several months, or until the desired result is effected or a significant diminution in the size and/or number of the lesions is achieved. In general, it is contemplated that the formulation will be applied one to four times daily. With a skin patch or occlusive dressing, the device is generally maintained in place on the body surface throughout a drug delivery period, typically in the range of 8 to 72 hours, and replaced as necessary.

In a preferred embodiment of the invention the ingenol compounds are administered, i.e. applied, topically at the site of the lesion, for example, over the whole or partial surface area of the lesion. The ingenol compounds may be topically applied in any suitable form including solutions, emulsions (oil-in-water, water-in-oil, aerosols or foams), ointments, pastes, lotions, powders, paints, gels, hydrogels, hydrocolloids and creams may be prepared so as to contain liposomes, micelles, and/or microspheres. Suitable carriers or additives include mineral oil, propylene glycol, polyoxyethylene, polyoxypropylene, emulsifying wax, sorbitan monostearate, polysorbate 60, cetyl esters wax, cetearyl alcohol, 2-octyldodecanol, cyclodextrin, isopropyl alcohol, ethanol, benzyl alcohol and water. Alternatively, the ingenol compounds may be presented in the form of an active occlusive dressing, i.e. where the ingenol compound is impregnated or coated on a dressing such as bandages, gauzes, tapes, nets, adhesive plaster, films, membranes or patches.

The formulation of compositions and dressings contemplated herein is well known to those skilled in the art, see for example, *Remington's Pharmaceutical Sciences*, 18$^{th}$ Edition, Mack Publishing, 1990. Compositions may contain any suitable carriers, diluents or excipients. These include all conventional solvents, dispersion media, fillers, solid carriers, coatings, antifungal and antibacterial agents, viscosity enhancers, film formers, dermal penetration agents, surfactants, isotonic and absorption agents and the like. The carrier for compositions contemplated by the present invention must be pharmaceutically acceptable in the sense of being compatible with the other ingredients of the composition and not injurious to the subject.

Formulations of the invention may optionally contain a pharmaceutically acceptable viscosity enhancer and/or film former. A viscosity enhancer increases the viscosity of the formulation so as to inhibit its spread beyond the site of application. A film former, when it dries, forms a protective film over the site of application. The film inhibits removal of the active ingredient and keeps it in contact with the site being treated. Solutions that dry to form a film are sometimes referred to as paints.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight.

Creams, are also well known in the art, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

As will be appreciated by those working in the field of pharmaceutical formulation, gels are semisolid, suspension-type systems. Single-phase gels contain gelling agents distributed substantially uniformly throughout the carrier liquid, which is typically aqueous, but also, preferably, contain an alcohol such as isopropyl alcohol, and, optionally, an oil.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. It is generally necessary that the insoluble matter in a lotion be finely divided. Lotions will typically contain suspending agents to produce better dispersions as well as compounds useful for localizing and holding the active agent in contact with the skin.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

In one embodiment of the invention, the ingenol compound is topically applied in the form of an isopropyl alcohol-based gel. One suitable formulation includes isopropyl alcohol, benzyl alcohol, a cellulose polymer, such as hydroxyethyl cellulose and buffer (e.g. citrate) at a pH<3. In another embodiment of the invention, the ingenol compound can be formulated for topical application in the form of a macrocetyl ether cream, for example containing cetomacrogel emulsifying wax, white soft paraffin and liquid paraffin.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the invention include cationic (positively charged), anionic (negatively charged) and neutral preparations.

Micelles are known in the art to be comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids. Preparation of microspheres is well known in the art and described in the pertinent texts and literature.

It will be understood that the invention may also be practiced in conjunction with the use of other supplementary therapies such as those mentioned hereinabove or (M. M. Lipke, *Clinical Medicine & Research*, 2006, 4, 273-293). If appropriate, additional agents may be formulated into a composition or dressing together with the ingenol compound or they can be administered separately.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

The compounds of the invention may also be presented for use in veterinary compositions. These may be prepared by any suitable means known in the art. Examples of such compositions include those adapted for topical application e.g. creams, ointments, gels, lotions etc as described above.

The invention will now be described with reference to the following Examples which are included for the purpose of illustrating certain embodiments of the invention and are not to be considered as limiting the generality hereinbefore described.

EXAMPLES

Example 1

Efficacy of Ingenol-3-angelate (PEP005) Topical Gel in a Cottontail Rabbit Papilloma Virus (CRPV) model of cutaneous warts in Hra(NZW)SPF New Zealand White Rabbits.
Methods The New Zealand White [Hra(NZW)SPF] rabbit was selected as the Test System because: 1) it is a species that is susceptible to transfection by CRPV plasmid DNA; and 2) this species has been demonstrated to develop cutaneous warts in response to inoculation (Christensen N D, Kreider J W. Animal models of papillomavirus infections. Ch 25. In: Zak O, Sande M A, editors. Handbook of animal models of infection. New York: Academic Press; 1999. p. 1039-47). Concentrations of the inoculant were selected empirically based on published information for the CRPV model in which cutaneous papillomas (warts) were induced in rabbits (Christensen N D. Cottontail rabbit papillomavirus (CRPV) model system to test antiviral and immunotherapeutic strategies. Antiviral chemistry & chemotherapy 2005; 16(6):355-62). The percutaneous route was selected because this route has been successfully used to establish cutaneous papilloma (wart) formation in rabbits following inoculation with CRPV DNA.

Ten female Hra:(NZW)SPF New Zealand White (NZW) female rabbits were randomly assigned to four dose groups, three rabbits per dose group in Groups 1 through 3 and one rabbit in Group 4.

Four days before inoculation (DS-4), the backs of the rabbits were shaved over an area encompassing all eight exposure sites using an electric clipper with an appropriate blade. Following clipping, the skin was chemically depilated with Veet® (distributed by Reckitt Benckiser Inc., Parsippany, N.J., USA). The clipped area (approximately 10 cm×20 cm) extended from the shoulders to the hip joints of each rabbit and was approximately 10 cm wide (extending ventrolaterally from the dorsal midline approximately 5 cm on each side). Any re-growth of hair was carefully clipped, as needed throughout the study.

Three days before inoculation, rabbits were anesthetized with isoflourane/oxygen and the exposure sites on each rabbit were tattooed (Aims Black Pigment #242, AIMS Inc, Piscataway, N.J., USA, lot number F0707A, expiration date 30 Jun. 2008) on either side of each inoculation site. Each exposure site was carefully scarified using a scalpel blade (#60) to create a brush burn-like lesion in order to promote wart growth following inoculation. Rabbits were monitored constantly for signs of regular breathing and comfort while anesthetized and until full recovery from anesthesia.

Eight approximately-equal areas on the dorsum (areas A, B, C, D, E, F, G, and H; areas A and B being closest to the shoulders, areas C, D, E, and F in the middle, and areas G and H closest to the tail) were inoculated. All ten female rabbits were inoculated once on DS 1. Rabbits were anesthetized with isoflourane/oxygen and given a single dose of CRPV plasmid DNA by percutaneous administration, at eight independent skin sites per rabbit. Viral inoculations were made by scratching approximately 16.7 µL of the inoculant into the scarified site (approximately 15 scratches per site) with a 25 gauge needle.

Following inoculation, each of the eight sites per rabbit was observed for development of warts once weekly for three weeks. Daily observations for development of the warts began during week 4 and continued until the first day of test article or placebo administration. The length and width of each cutaneous wart was recorded from the day of first observation to the completion of the study.

Dose administration of PEP005 Topical Gel or placebo began on DS 50. On the day prior to initiation of dosing, four warts (treatment sites) of similar sizes were selected for dosing on each rabbit; 3 sites were designated as PEP005 Topical Gel sites and 1 site was identified as placebo control. The treatment area of each dosing site was determined from the most recent length and width measurements of each wart ($mm^2$). Concentrations of 0 (placebo), 0.01, 0.1 or 0.25% PEP005 Topical Gels were administered at a constant volume of 0.5 µL/$mm^2$ (0, 0.05, 0.5 or 1.25 µg/$mm^2$). The dosing regimen is summarised in Table 1.

TABLE 1

| Dose Group | Dose (µg/$mm^2$) | Concentration (%) | Application Volume (µcL/$mm^2$) | Number of Rabbits | Assigned Rabbit Numbers |
|---|---|---|---|---|---|
| 1 | 0/0.05 | 0/0.01[a] | 0.5 | 3 | 7591-7593 |
| 2 | 0/0.5 | 0/0.1[a] | 0.5 | 3 | 7594-7596 |
| 3 | 0/1.25 | 0/0.25[a] | 0.5 | 3 | 7597-7599 |

TABLE 1-continued

| Dose Group | Dose (μg/mm²) | Concentration (%) | Application Volume (μcL/mm²) | Number of Rabbits | Assigned Rabbit Numbers |
|---|---|---|---|---|---|
| 4 | 0/0.05/ 0.5/1.25 | 0/0.01/ 0.1/0.25[b] | 0.5 | 1 | 323 |

[a] One site for placebo and three sites per test article concentration.
[b] One site for placebo and one of each of three sites per test article concentration.

For Groups 1 through 3, a single concentration of PEP005 Topical Gel was applied to two sites for three days (DS 50 to 52) and the third site received the same concentration of PEP005 Topical Gel for five days (DS 50 to 54). Placebo gel was administered to a separate placebo control site for five days (DS 50 to 54). For Group 4, each concentration of PEP005 Topical Gel was administered to a single site for five days (DS 50 to 54) on one rabbit. Placebo gel was administered to a separate placebo control site for five days (DS 50 to 54). For each dose application, within each treatment site the gel was uniformly applied to the skin surface around the base of the wart using a calibrated pipette.

Each of the four dosed sites on each rabbit was examined daily during the dosing period (immediately prior to each dose application) and for the first two weeks of the post-dosing period. Examinations for the remainder of the post-dosing period were performed on Monday, Wednesday and Friday. On each occasion the length and width of each treated wart was measured and recorded.

Treated skin sites were observed daily (immediately prior to each dose application) for signs of skin irritation (erythema, edema, eschar) during the dosing period and for at least four weeks postdosea. Skin irritation scores were evaluated using the following criteria:

| | Grade |
|---|---|
| Erythema/Eschar Scoring | |
| No erythema[a] | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Edema Scoring | |
| No edema[a] | 0 |
| Very slight edema (barely perceptible) | 1 |
| Slight edema (edges of area well-defined by definite raising) | 2 |
| Moderate edema (edges raised approximately 1 mm) | 3 |
| Severe edema (raised more than 1 mm and extending beyond the dermal test sites) | 4 |

The surface areas of each wart selected for treatment were calculated (as a standard ellipse [length×width×π]) based on the daily measurements obtained from one week prior to dosing initiation continuing through the study period. Weekly average surface area measurements were calculated for each individual wart. Beginning with the first week post-dosing, the percent change from the predose average measurement was calculated for each PEP005 Topical Gel treated and Placebo treated wart for each rabbit in each dose group.

The respective compositions for 0.25% w/w, 0.10% w/w, 0.01% w/w PEP005 and placebo gels are given below in Table 2:

TABLE 2

| Gel Formulations | 0.25% | 0.10% | 0.01% | Placebo |
|---|---|---|---|---|
| PEP005 | 0.25 | 0.10 | 0.01 | — |
| Benzyl alcohol | 0.90 | 0.90 | 0.90 | 0.90 |
| Citrate buffer, pH 2.75 | 67.35 | 67.50 | 67.59 | 67.60 |
| Isopropyl alcohol | 30.00 | 30.00 | 30.00 | 30.00 |
| Hydroxyethyl cellulose (HX Grade) | 1.50 | 1.50 | 1.50 | 1.50 |
| TOTAL | 100 | 100 | 100 | 100 |

Results

Within each group, two of the four chosen warts on each rabbit were treated with PEP005 Topical Gel daily for 3 days (3D), one site was treated for 5 consecutive days (5D) and the fourth site was administered placebo gel for daily for 5 days to serve as the control site. The results are depicted below, where the text tables describe the weekly average percent change (±standard deviation) of wart surface area following treatment as compared to the predose wart area (week immediately prior to dosing initiation) for each rabbit.

PEP005 Gel 0.01%

Rabbit 7591

Treatment:
   3D (DSs 50-52) Sites B and E
   5D (DSs 50-54) Site A, Site F (placebo)
   No skin reactions occurred at the Placebo site.

All three sites treated with PEP005 Topical Gel showed erythema grade 1 on DSs 52 to 54.

Average percent change of wart size at Site A (5D) was slightly decreased during the week of dose administration as compared to the Placebo treated wart (Site F). A trend of growth retardation (as evaluated from the average percent change) was apparent for this wart for the remainder of the evaluation period as compared to the growth trends of the Placebo and other PEP005 Topical Gel treated warts. The results are depicted in Table 3 where data is presented as a percentage change of wart area relative to DSs 50.

TABLE 3

| | Rabbit 7591 Group I 0.01% | | | |
|---|---|---|---|---|
| DSs* | Site F (5 D) Placebo | Site B (3 D) | Site E (3 D) | Site A (5 D) |
| 51-57 | 0.3 ± 15.1 | 36.1 ± 47.2 | 12.0 ± 11.7 | −1.7 ± 19.0 |
| 58-64 | 27.9 ± 28.0 | 86.0 ± 99.7 | 17.9 ± 12.6 | 24.9 ± 16.5 |
| 66-72 | 86.0 ± 13.4 | 128.4 ± 48.3 | 69.9 ± 41.1 | 49.2 ± 9.1 |
| 74-81 | 309.4 ± 122.7 | 337.7 ± 98.8 | 350.0 ± 131.9 | 125.7 ± 61.0 |
| 84-95 | 286.7 ± 76.1 | 713.6 ± 221.5 | 328.4 ± 52.0 | 133.8 ± 48.1 |

*Number of days after viral innoculation

Rabbit 7592

Treatment:
   3D (DSs 50-52) Sites E and F
   5D (DSs 50-54) Site G, Site A (placebo)
   No skin reactions occurred at the Placebo site.

All three PEP005 Topical Gel dosed sites had erythema and edema grades 1 between DSs 51 to 57.

Average percent change of wart size at Site G (5D) was slightly decreased during the week of dose administration as compared to the Placebo group (Site A). The results are depicted in Table 4 where data is presented as a percentage change of wart area relative to DSs 50.

TABLE 4

| | Rabbit 7592 Group I 0.01% | | | |
|---|---|---|---|---|
| DSs* | Site A (5 D) Placebo | Site E (3 D) | Site F (3 D) | Site G (5 D) |
| 51-57 | 14.9 ± 11.7 | 14.4 ± 6.8 | 10.5 ± 27.7 | 2.5 ± 5.94 |
| 58-64 | -2.6 ± 11.6 | 46.9 ± 10.2 | 18.8 ± 10.7 | 18.0 ± 10.4 |
| 66-72 | 38.0 ± 4.4 | 95.6 ± 17.3 | 48.3 ± 0.7 | 67.6 ± 10.8 |
| 74-81 | 43.8 ± 13.0 | 134.9 ± 15.4 | 74.2 ± 28.0 | 92.6 ± 6.7 |
| 84-95 | 98.4 ± 26.8 | 120.8 ± 13.7 | 103.6 ± 36.5 | 104.8 ± 21.3 |

*Number of days after viral innoculation

Rabbit 7593
Treatment:
  3D (DSs 50-52) Sites A and D
  5D (DSs 50-54) Site F, Site E (placebo)
  No skin reactions occurred at the Placebo site.
  All three PEP005 Topical Gel dosed sites had erythema and edema grade 1 between DSs 51 and 57. Site D erythema scores increased to grade 2 on DSs 52 to 54, 56 and 57.
  Average percent change of wart size in Sites D and A (5D) was slightly decreased during the week of dose administration as compared to the Placebo site (E). Wart growth was retarded (as evaluated from the average percent change) at Site D wart the week following dose administration. The results are depicted in Table 5 where data is presented as a percentage change of wart area relative to DSs 50.

TABLE 5

| | Rabbit 7593 Group I 0.01% | | | |
|---|---|---|---|---|
| DSs* | Site E (5 D) Placebo | Site D (3 D) | Site F (3 D) | Site A (5 D) |
| 51-57 | 31.4 ± 29.2 | -0.7 ± 7.4 | 33.0 ± 32.4 | 11.5 ± 24.4 |
| 58-64 | 83.6 ± 14.5 | 13.2 ± 11.5 | 69.3 ± 28.1 | 76.4 ± 22.3 |
| 66-72 | 128.9 ± 11.4 | 94.5 ± 47.0 | 169.0 ± 55.2 | 214.0 ± 52.5 |
| 74-81 | 190.2 ± 50.4 | 190.0 ± 55.5 | 275.9 ± 87.3 | 354.4 ± 125.4 |
| 84-95 | 328.5 ± 106.3 | 206.3 ± 52.7 | 291.6 ± 35.3 | 627.2 ± 119.6 |

*Number of days after viral innoculation

PEP005 Gel 0.1%
Rabbit 7594
Treatment:
  3D (DSs 50-52) Sites A and C
  5D (DSs 50-54) Site E, Site B (placebo)
  No skin reactions occurred at the Placebo site.
  All three PEP005 Topical Gel dosed sites had erythema and edema grade 1 during the first week of study. At site A, erythema increased to grade 2 on DSs 53 and 54, and also at Site C on DSs 53 and 54. Flaking grade 1 or 2 was observed at PEP005 Topical Gel treated sites two weeks after dosing (DSs 65 to 67).
  Average percent change in wart size at Sites A and E (5D) was slightly decreased during the week following dose administration as compared to the Placebo site. The results are depicted in Table 6 where data is presented as a percentage change of wart area relative to DSs 50.

TABLE 6

| | Rabbit 7594 Group II 0.1% | | | |
|---|---|---|---|---|
| DSs* | Site B (5 D) Placebo | Site A (3 D) | Site C (3 D) | Site E (5 D) |
| 51-57 | 15.5 ± 9.9 | 5.4 ± 10.9 | 14.2 ± 11.7 | 17.0 ± 19.4 |
| 58-64 | 36.3 ± 4.3 | -9.3 ± 19.4 | 28.3 ± 10.9 | -1.0 ± 34.1 |

TABLE 6-continued

| | Rabbit 7594 Group II 0.1% | | | |
|---|---|---|---|---|
| DSs* | Site B (5 D) Placebo | Site A (3 D) | Site C (3 D) | Site E (5 D) |
| 66-72 | 39.2 ± 33.3 | 59.7 ± 43.9 | 64.6 ± 26.0 | 53.8 ± 51.2 |
| 74-81 | 40.0 ± 11.9 | 102.3 ± 67.2 | 129.2 ± 46.0 | 77.0 ± 39.0 |
| 84-95 | 68.6 ± 28.5 | 149.6 ± 49.4 | 185.4 ± 41.4 | 137.2 ± 46.0 |

*Number of days after viral innoculation

Rabbit 7595
Treatment:
  3D (DSs 50-52) Sites F and G
  5D (DSs 50-54) Site H, Site D (placebo)
  Dermal flaking (grade 1) was observed at the Placebo treated site on DSs 69 to 74.
  All three PEP005 Topical Gel dosed sites showed erythema grade 1 during the first two or three days of dosing, and erythema grade 2 was observed for the remainder of the dosing week and/or into the week following dosing. During the $3^{rd}$ post-dosing week, the severity of erythema declined to grade 1. Edema grade 1 was also observed at all three PEP005 Topical Gel treated sites during the week of dosing and was persistent through DS 58 at Site H (5D). At site Site G (3D) the initial grade 1 edema increased to grade 3 on DS 54 then declined to grade 1 and persisted until DS 58. Flaking (grade 1 or 2) was observed at Sites G and H two weeks after dosing (generally DSs 65 to 74).
  The average percent change in wart size at Site G was decreased during the week of, and the week following, dosing as compared to the Placebo group. Average percent change in wart size at Site H was decreased during the week of dosing. The results are depicted in Table 7 where data is presented as a percentage change of wart area relative to DSs 50.

TABLE 7

| | Rabbit 7595 Group II 0.1% | | | |
|---|---|---|---|---|
| DSs* | Site D (5 D) Placebo | Site F (3 D) | Site G (3 D) | Site H (5 D) |
| 51-57 | -1.1 ± 10.3 | 10.6 ± 11.6 | -16.6 ± 8.0 | -14.5 ± 28.7 |
| 58-64 | 15.4 ± 11.8 | 55.3 ± 42.5 | -22.1 ± 10.2 | 12.6 ± 25.0 |
| 66-72 | 43.4 ± 11.1 | 203.5 ± 40.2 | 47.9 ± 35.9 | 132.0 ± 53.9 |
| 74-81 | 69.9 ± 34.3 | 327.5 ± 106.9 | 123.9 ± 67.7 | 271.0 ± 91.9 |
| 84-95 | 161.5 ± 20.9 | 340.0 ± 82.3 | 179.9 ± 26.2 | 355.8 ± 28.9 |

*Number of days after viral innoculation

Rabbit 7596
Treatment:
  3D (DSs 50-52) Sites B and F
  5D (DSs 50-54) Site C, Site D (placebo)
  Erythema grade 1 was observed at the Placebo site DSs 50 to 52 and edema grade 1 was noted from DSs 69 to 74.
  Erythema grade 1 was observed at all three PEP005 Topical Gel treated sites during the first three days of dosing increasing in severity to grade 2 on DSs 53 and 54. Erythema grade 1 was generally observed to persist until DS 82 with Site B (3D) showing an increase in severity of erythema (grade 2) from DSs 64 to 72. Edema grade 1 was generally observed at all PEP005 Topical Gel treated sites from DS 52 or 53 until DS 82, with edema grade 2 occurring at Site B on DS 69. Flaking grade 1 was noted at all PEP005 Topical Gel dosed sites the week following the completion of dosing. Additionally, eschar formation was observed at Site C (5D) on DS 59 following the loss of the wart.

The Placebo treated wart was lost (spontaneously detached) on DS 53 following three dose administrations. The warts at the sites treated with PEP005 Topical Gel for three days (sites B and F) and 5 days (site C) detached on DSs 60, 64 and 59, respectively. Notably, the initial size of these warts were smaller in comparison with the warts on other rabbits with the exception of Rabbit 323. The starting surface areas, calculated as a standard ellipse, of the warts were 6.3, 84.8, 75.5 and 25.1 mm² for Sites D (placebo), B, F and C, respectively. The results are depicted in Table 8 where data is presented as a percentage change of wart area relative to DSs 50.

TABLE 8

Rabbit 7596 Group II 0.1%

| DSs* | Site D (5 D) Placebo | Site B (3 D) | Site F (3 D) | Site C (5 D) |
|---|---|---|---|---|
| 51-57 | −25.0 ± 35.6 | 7.9 ± 31.2 | −9.1 ± 16.8 | 49.9 ± 47.8 |
| 58-64 | Lost | −48.1 ± 10.5 | −32.0 ± 39.6 | 0.0 ± 0.0 |
| 66-72 | N/A | Lost | Lost | Lost |

*Number of days after viral innoculation

The average change in wart size relative to pre-dose week for warts treated with PEP005 0.1% for placebo, 3 day and 5 day treatments is summarised below in Table 9. Data is presented as percentage change of wart area relative to Day 50.

TABLE 9

Average percentage change in wart area for placebo, 3 day and 5 day treatments with 0.1% PEP005

| Days | Placebo | 3 day | 5 day |
|---|---|---|---|
| 51-57 | 8.1 | 2.1 | 17.5 |
| 56-64 | 25.8 | −4.7 | 3.9 |

PEP005 Gel 0.25%
Rabbit 7597
Treatment:
  3D (DSs 50-52) Sites E and F
  5D (DSs 50-54) Site C, Site G (placebo)

Flaking grade 1 or grade 2 was observed at the Placebo treated site on DSs 61 to 73, and erythema grade 2 (DSs 52 to 54; 56 to 58), erythema grade 1) (DSs 59 to 65) and edema grade 2 (DSs 52 to 54) were also noted.

On the first day of dosing (DS 50) grade 1 erythema was noted following treatment at all three PEP005 Topical Gel treated sites. Grade 2 erythema was observed at all three PEP005 Topical Gel dosed sites during the week of dosing [DSs 51 to 54 and DSs 56 and 57 (Site C only)]. At Site F (3D), the erythema grade 2 response persisted through DSs 58 to 62 while all other sites, including in the Placebo, were generally observed with erythema grade 1. Edema grade 1 was noted at all three PEP005 Topical Gel dosed sites on the first and/or second days of dosing. Edema grade 2 was observed at Site E (3D) and edema grade 3 at Sites F (3D) and C (5D) for the remainder of the dosing period. Flaking grades 1 or 2 were observed at all PEP005 Topical Gel treated sites between one and two weeks after dosing (generally DSs 61 to 73).

Average percent change in wart sizes at PEP005 Topical Gel dosed sites were generally decreased during the week of, and during the three weeks following, dosing as compared to the Placebo treated site. The results are depicted in Table 10 where data is presented as a percentage change of wart area relative to DSs 50.

TABLE 10

Rabbit 7597 Group III 0.25%

| DSs* | Site G (5 D) Placebo | Site E (3 D) | Site F (3 D) | Site C (5 D) |
|---|---|---|---|---|
| 51-57 | 27.6 ± 42.7 | −3.9 ± 9.9 | −27.6 ± 13.7 | −21.5 ± 11.9 |
| 58-64 | 25.3 ± 31.1 | −11.1 ± 33.8 | −5.2 ± 43.9 | −19.9 ± 29.8 |
| 66-72 | 175.5 ± 57.6 | 123.7 ± 20.7 | 136.6 ± 41.1 | 110.0 ± 48.6 |
| 74-81 | 434.3 ± 203.7 | 281.6 ± 113.7 | 252.2 ± 93.5 | 175.5 ± 62.9 |
| 84-95 | Merged with E | 786.3 ± 315.8 | 311.6 ± 38.4 | 249.9 ± 22.4 |

*Number of days after viral innoculation

Rabbit 7598
Treatment:
  3D (DSs 50-52) Sites E and H
  5D (DSs 50-54) Site C, Site G (placebo)

Erythema grade 1 was observed at the Placebo site on DSs 64 and 65.

All three PEP005 Topical Gel dosed sites responded with erythema grade 1 or grade 2 during the week of dosing continuing into the week following dosing [DSs 58 and 59 and DSs 60 to 62 (Site C only)]. Edema grades 2 or 3 were also observed on DSs 53 and/or 54 with lower grade (1 or 2) edema generally persisting at Site C (5D) until DS 59.

Average percent change of wart sizes in PEP005 Topical Gel dosed groups were increased throughout the study as compared to the Placebo group. The results are depicted in Table 11 where data is presented as a percentage change of wart area relative to DSs 50.

TABLE 11

Rabbit 7598 Group III 0.25%

| DSs* | Site G (5 D) Placebo | Site E (3 D) | Site H (3 D) | Site C (5 D) |
|---|---|---|---|---|
| 51-57 | −23.7 ± 13.2 | −21.7 ± 23.4 | 18.4 ± 31.2 | 13.1 ± 16.5 |
| 58-64 | −15.5 ± 4.5 | 0.1 ± 32.1 | 115.9 ± 110.3 | 92.1 ± 47.3 |
| 66-72 | 5.9 ± 18.5 | 152.9 ± 83.5 | 503.4 ± 153.2 | 274.0 ± 107.8 |
| 74-81 | 28.6 ± 41.2 | 295.4 ± 124.8 | 848.6 ± 292.5 | 379.7 ± 100.6 |
| 84-95 | 95.8 ± 48.7 | 748.6 ± 180.3 | 1718.1 ± 292.4 | 577.9 ± 105.0 |

*Number of days after viral innoculation

Rabbit 7599
Treatment:
  3D (DSs 50-52) Sites D and E
  5D (DSs 50-54) Site H, Site B (placebo)

No skin reactions were observed at the Placebo gel treated site.

All three PEP005 Topical Gel dosed sites showed erythema grade 1 or 2 during the week of dosing and edema grades 1 or 2 from DSs 52 to 54. The wart at Site D (3D) was also observed with grade 2 flaking from DSs 69 to 73. The results are depicted in Table 12 where data is presented as a percentage change of wart area relative to DSs 50.

TABLE 12

Rabbit 7599 Group III 0.25%

| DSs* | Site B (5 D) Placebo | Site D (3 D) | Site E (3 D) | Site H (5 D) |
|---|---|---|---|---|
| 51-57 | 32.9 ± 29.7 | 3.6 ± 57.6 | 8.2 ± 57.7 | 60.0 ± 36.2 |
| 58-64 | 35.6 ± 27.6 | 2.0 ± 26.4 | 64.3 ± 116.5 | 140.8 ± 86.0 |

TABLE 12-continued

| | Rabbit 7599 Group III 0.25% | | | |
|---|---|---|---|---|
| DSs* | Site B (5 D) Placebo | Site D (3 D) | Site E (3 D) | Site H (5 D) |
| 66-72 | −6.3 ± 51.9 | 69.8 ± 15.0 | 410.5 ± 125.2 | 432.4 ± 42.9 |
| 74-81 | 32.5 ± 60.5 | 171.3 ± 77.5 | 660.1 ± 229.2 | 673.2 ± 149.7 |
| 84-95 | 113.1 ± 48.4 | 355.1 ± 47.7 | 779.0 ± 254.5 | 837.9 ± 76.4 |

*Number of days after viral innoculation

PEP0005 Gel 0.05, 0.1 and 0.25%
4.5.1. Rabbit 323
Treatment:
    5 Days at all sites (DSs 50-54)
    Placebo Site G; 0.01% Site B; 0.1% Site F; 0.25% Site H
    Grade 1 erythema was observed at the Placebo treated site on DS 63.

Erythema grade 2 was noted at all three PEP005 Topical Gel dosed sites during the week of dosing. Erythema grade 1 was observed at Sites F and H (0.1% and 0.25%, respectively) on DS 51 and during the week following dosing and at Site B (0.01%) on DSs 69 and 73. Edema was also observed at all three PEP005 Topical Gel dosed sites on DSs 52 and 56 to 58 (grade 1) and on DSs 53 to 54 (grade 2). The results are depicted in Table 13 where data is presented as a percentage change of wart area relative to DSs 50.

TABLE 13

| | Rabbit 323 | | | |
|---|---|---|---|---|
| DSs* | Site G (5 D) Placebo | Site B (3 D) 0.01% | Site F (3 D) 0.1% | Site H (5 D) 0.25% |
| 51-57 | −38.1 ± 23.0 | −42.9 ± 23.5 | 9.5 ± 51.1 | 128.6 ± 90.6 |
| 58-64 | 73.8 ± 93.7 | 117.9 ± 92.0 | 557.1 ± 493.6 | 864.3 ± 736.4 |
| 66-72 | 333.3 ± 91.3 | 450.0 ± 52.3 | 1864.4 ± 230.2 | 2955.0 ± 491.9 |
| 74-81 | 691.7 ± 453.9 | 1071.9 ± 533.2 | 3233.3 ± 1986.8 | 4906.3 ± 1197.1 |
| 84-95 | 1358.3 ± 165.6 | 1803.1 ± 158.7 | 5494.4 ± 754.3 | 7133.3 ± 378.0 |

*Number of days after viral innoculation

The invention claimed is:

1. A method for treating a virally-induced wart on a subject in need of virally-induced wart treatment, the method comprising:
    topically applying a therapeutically effective amount of a pharmaceutical composition consisting of a single ingenol angelate compound, a pharmaceutically acceptable carrier, and optionally at least one additive to the virally-induced wart on the subject for treatment of the virally-induced wart on the subject,
    wherein the virally-induced wart is induced by a Human Papilloma Virus (HPV), the single ingenol angelate compound is ingenol-3-angelate or a pharmaceutically acceptable salt, racemate or stereoisomer thereof or any mixture thereof, and the single ingenol angelate compound is present in the pharmaceutical composition in an amount of from about 0.01% to about 0.2% by weight.

2. The method of claim 1, wherein the HPV is selected from an HPV group consisting of HPV 1, HPV 2, HPV 3, HPV 4, HPV 5, HPV 7, HPV 8, HPV 9, HPV 10, HPV 11, HPV 12, HPV 14, HPV 15, HPV 17, HPV 19, HPV 20, HPV 21, HPV 22, HPV 23, HPV 24, HPV 25, HPV 26, HPV 27, HPV 28, HPV 29, HPV 30, HPV 36, HPV 37, HPV 38, HPV 41, HPV 42, HPV 43, HPV 44, HPV 45, HPV 46, HPV 47, HPV 49, HPV 50, HPV 51, HPV 52, HPV 54, HPV 57, HPV 63, and HPV 65.

3. The method of claim 1, wherein the HPV is selected from an HPV group of HPVs consisting of HPV 6, HPV 11, HPV 30, HPV 42, HPV 43, HPV 44, HPV 45, HPV 51, HPV 52 and HPV 54.

4. The method of claim 1, wherein the virally-induced wart is selected from the group consisting of common warts, plane or flat warts, myrmecia, plantar warts, butcher's warts, mosaic warts, filiform warts, periungual warts, anogenital warts, oral warts, senile warts, digitate warts and palmar warts.

5. The method of claim 1, wherein the virally-induced wart is a genital wart.

6. The method according to claim 1, wherein the single ingenol angelate compound is fully or partially chemically synthesized.

7. The method according to claim 1, wherein the single ingenol angelate compound is isolated from a species of the Euphorbiaceae family.

8. The method according to claim 1, wherein the pharmaceutical composition further consists of one or more additives.

9. The method according to claim 1, wherein the composition is an isopropyl alcohol gel or a macrocetyl ether cream.

10. The method according to claim 1, wherein the subject is human.

11. The method according to claim 10, wherein the virally-induced wart is located on the subject in an anatomical area selected from a group consisting of head, face, nose, muzzle, mouth, a lip, neck, shoulder, back, a leg, a knee, a foot, a hand an elbow, penis and vulva.

12. The method according to claim 10, wherein the virally-induced wart is located on a genital or anus.

13. The method according to claim 9, wherein the composition is an isopropyl alcohol gel.

14. The method of claim 1, wherein the virally-induced wart is selected from the group consisting of common warts, planar warts and flat warts.

15. The method according to claim 7, wherein the single ingenol angelate compound is isolated from *Euphorbia peplus*.

16. The method according to claim 1, wherein the step of topically applying the single ingenol angelate compound to the virally-induced wart on the subject includes applying the single ingenol angelate compound to the area surrounding the virally-induced wart.

17. The method according to claim 1, wherein the step of topically applying the single ingenol angelate compound to the virally-induced wart on the subject comprises topically applying the single ingenol angelate compound over the whole or partial surface area of the virally-induced wart.

18. The method according to claim 17, wherein the surface area of the virally-induced wart is greater than about 500 mm$^2$.

19. The method according to claim 17, wherein the surface area of the virally-induced wart is greater than about 1000 mm².

20. The method according to claim 17, wherein the surface area of the virally-induced wart is about 250 mm² or less.

21. The method according to claim 17, wherein the surface area of the virally-induced wart is about 150 mm² or less.

22. The method according to claim 17, wherein the surface area of the virally-induced wart is about 100 mm² or less.

23. The method according to claim 17, wherein the surface area of the virally-induced wart is about 75 mm² or less.

24. The method according to claim 17, wherein the surface area of the virally-induced wart is about 50 mm² or less.

25. The method according to claim 17, wherein the surface area of the virally-induced wart is about 25 mm² or less.

26. The method according to claim 17, wherein the surface area of the virally-induced wart is about 10 mm² or less.

27. The method according to claim 1, wherein the single ingenol angelate compound is in crystalline form.

28. The method according to claim 1, wherein the single ingenol angelate compound is applied topically to and/or around the cutaneous lesion on the subject once daily.

29. The method according to claim 13, wherein the isopropyl alcohol gel is applied to and/or around the cutaneous lesion on the subject once daily.

30. The method according to claim 1, wherein the si g ingenol angelate compound is applied to and/or around the cutaneous lesion one to four times daily.

31. The method according to claim 13, wherein the isopropyl alcohol gel is applied to and/or around the cutaneous lesion one to four times daily.

32. A method for treating a cutaneous lesion caused by a virus on a subject in need of cutaneous lesion treatment, the method comprising:
topically applying a pharmaceutical composition consisting of a single ingenol angelate compound, a pharmaceutically acceptable carrier, and optionally at least one additive to and/or around the cutaneous lesion on the subject in accordance with a dose regimen for treatment of the cutaneous lesion on the subject,
wherein the single ingenol angelate compound is ingenol-3-angelate or a pharmaceutically acceptable salt, racemate or stereoisomer thereof or any mixture thereof,
wherein the cutaneous lesion is caused by a Human Papilloma Virus (HPV), and
wherein the single ingenol angelate compound is present in the pharmaceutical composition in an amount of from about 0.01% to about 0.2% by weight.

33. The method according to claim 32, wherein the single ingenol angelate compound is present in the pharmaceutical composition in an amount by weight selected from a group of amounts by weight consisting of about 0.025%, about 0.05%, about 0.075%, about 0.125%, about 0.15%, and about 0.2%.

34. The method according to claim 32, wherein the single ingenol angelate compound is present in the pharmaceutical composition in an amount of about 0.01% by weight.

35. The method according to claim 32, wherein the single ingenol angelate compound is present in the pharmaceutical composition in an amount of about 0.1% by weight.

36. The method according to claim 32, wherein the pharmaceutical composition is applied topically to and/or around the cutaneous lesion on the subject once daily.

37. The method according to claim 32, wherein the pharmaceutical composition is applied to and/or around the cutaneous lesion on the subject once daily.

38. The method according to claim 32, wherein the pharmaceutical composition is applied to and/or around the cutaneous lesion one to four times daily.

39. The method according to claim 32, wherein the pharmaceutical composition is applied to and/or around the cutaneous lesion one to four times daily.

40. The method according to claim 34, wherein the pharmaceutical composition is applied topically to and/or around the cutaneous lesion on the subject daily for three consecutive days.

41. The method according to claim 35, wherein the pharmaceutical composition is applied topically to and/or around the cutaneous lesion on the subject daily for three consecutive days.

42. The method according to claim 34, wherein the pharmaceutical composition is applied topically to and/or around the cutaneous lesion on the subject daily for five consecutive days.

43. The method according to claim 35, wherein the pharmaceutical composition is applied topically to and/or around the cutaneous lesion on the subject daily for five consecutive days.

44. The method according to claim 32, wherein the pharmaceutical composition is a gel.

45. The method according to claim 32, wherein the at least one additive is benzyl alcohol.

46. The method according to claim 44, wherein the composition is an isopropyl alcohol gel.

47. The method according to claim 32, wherein the at least one additive is a buffer.

48. The method according to claim 47, wherein the buffer is a citrate buffer.

49. The method according to claim 32, wherein the at least one additive is a cellulose polymer.

50. The method according to claim 49, wherein the cellulose polymer is hydroxyethyl cellulose.

51. The method according to claim 32, wherein the pharmaceutical composition is applied to and/or around the cutaneous lesion one to four times daily.

52. The method according to claim 32, wherein the pharmaceutical composition is applied to and/or around the cutaneous lesion on the subject once daily.

53. The method according to claim 32, wherein the dose regimen comprises topically applying the pharmaceutical composition to and/or around the cutaneous lesion at least once daily for three consecutive days.

54. The method according to claim 32, wherein the dose regimen comprises topically applying the pharmaceutical composition to and/or around the cutaneous lesion at least once daily for five consecutive days.

55. The method according to claim 32, wherein the subject is a human.

56. The method of claim 32, wherein the HPV is selected from a group of HPVs consisting of HPV 1, HPV 2, HPV 3, HPV 4, HPV 5, HPV 7, HPV 8, HPV 9, HPV 10, HPV 11, HPV 12, HPV 14, HPV 15, HPV 17, HPV 19, HPV 20, HPV 21, HPV 22, HPV 23, HPV 24, HPV 25, HPV 26, HPV 27, HPV 28, HPV 29, HPV 30, HPV 36, HPV 37, HPV 38, HPV 41, HPV 42, HPV 43, HPV 44, HPV 45, HPV 46, HPV 47, HPV 49, HPV 50, HPV 51, HPV 52, HPV 54, HPV 57, HPV 63 and HPV 65.

57. The method of claim 32, wherein the HPV is selected from a group of HPVs consisting of HPV 6, HPV 11, HPV 30, HPV 42, HPV 43, HPV 44, HPV 45, HPV 51, HPV 52 and HPV 54.

58. The method of claim 55, wherein the cutaneous lesion is selected from the group consisting of common warts, plane or flat warts, myrmecia, plantar warts, butcher's warts, mosaic warts, filiform warts, periungual warts, anogenital warts, oral warts, senile warts, digitate warts and palmar warts.

59. The method of claim 55, wherein the cutaneous lesion is a genital wart.

60. The method of claim 55, wherein the cutaneous lesion is an anal wart.

61. The method according to claim 32, wherein the single ingenol angelate compound is in crystalline form.

62. A method for treating a cutaneous lesion caused by a virus on a subject in need of cutaneous lesion treatment, the method comprising:
topical application of a gel to the cutaneous lesion on the subject at least once daily in accordance with a dose regimen for treatment of the cutaneous lesion on the subject,
wherein the gel consists of a single ingenol angelate compound, benzyl alcohol, isopropyl alcohol, a buffer (citrate), and a cellulose polymer,
wherein the single ingenol angelate compound is ingenol-3-angelate or a pharmaceutically acceptable salt, racemate or stereoisomer thereof or any mixture thereof,
wherein the cutaneous lesion is caused by a Human Papilloma Virus (HPV), and
wherein the single ingenol angelate compound is present in the gel in an amount of from about 0.01% to about 0.2% by weight.

63. The method according to claim 62, wherein the gel has a formulation by weight as follows:
Ingenol-3-angelate 0.10%
Benzyl alcohol 0.90%
Citrate Buffer, pH 2.75 67.50%
Isopropyl alcohol 30.00%
Hydroxyethylcellulose 1.50%.

64. The method according to claim 62, wherein the gel has a formulation by weight as follows:
Ingenol-3-angelate 0.01%
Benzyl alcohol 0.90%
Citrate Buffer, pH 2.75 67.59%
Isopropyl alcohol 30.00%
Hydroxyethylcellulose 1.50%.

65. The method according to claim 62, wherein the step of topical application of the gel to the cutaneous lesion includes topically applying the gel to skin surface around the base of the wart.

66. The method according to claim 62, wherein the step of topical application of the gel to the cutaneous lesion includes topically applying the gel over the whole or partial surface area of the virally-induced wart.

67. The method according to claim 62, wherein the dose regimen is three consecutive days.

68. The method according to claim 62, wherein the dose regimen is five consecutive days.

69. The method according to claim 63, wherein the step of topical application of the gel to the cutaneous lesion includes topically applying the gel to skin surface around the base of the wart.

70. The method according to claim 63, wherein the step of topical application of the gel to the cutaneous lesion comprises topically applying the gel over the whole or partial surface area of the virally-induced wart.

71. The method according to claim 63, wherein the dose regimen is three consecutive days.

72. The method according to claim 63, wherein the dose regimen is five consecutive days.

73. The method according to claim 64, wherein the step of topical application of the gel to the cutaneous lesion includes topically applying the gel to skin surface around the base of the wart.

74. The method according to claim 64, wherein the step of topical application of the gel to the cutaneous lesion includes topically applying the gel over the whole or partial surface area of the virally-induced wart.

75. The method according to claim 64, wherein the dose regimen is three consecutive days.

76. The method according to claim 64, wherein the dose regimen is five consecutive days.

77. The method according to claim 62, wherein the subject is a human.

78. The method of claim 62, wherein the HPV is selected from a group of HPVs consisting of HPV 1, HPV 2, HPV 3, HPV 4, HPV 5, HPV 7, HPV 8, HPV 9, HPV 10, HPV 11, HPV 12, HPV 14, HPV 15, HPV 17, HPV 19, HPV 20, HPV 21, HPV 22, HPV 23, HPV 24, HPV 25, HPV 26, HPV 27, HPV 28, HPV 29, HPV 30, HPV 36, HPV 37, HPV 38, HPV 41, HPV 42, HPV 43, HPV 44, HPV 45, HPV 46, HPV 47, HPV 49, HPV 50, HPV 51, HPV 52, HPV 54, HPV 57, HPV 63 and HPV 65.

79. The method of claim 62, wherein the HPV is selected from a group of HPVs consisting of HPV 6, HPV 11, HPV 30, HPV 42, HPV 43, HPV 44, HPV 45, HPV 51, HPV 52 and HPV 54.

80. The method of claim 77, wherein the cutaneous lesion is selected from the group consisting of common warts, plane or flat warts, myrmecia, plantar warts, butcher's warts, mosaic warts, filiform warts, periungual warts, anogenital warts, oral warts, senile warts, digitate warts and palmar warts.

81. The method of claim 77, wherein the cutaneous lesion is a genital wart.

82. The method of claim 77, wherein the cutaneous lesion is an anal wart.

83. The method according to claim 62, wherein the dose regimen is three consecutive days.

84. The method according to claim 62, wherein the dose regimen is five consecutive days.

85. The method according to claim 62, wherein the single ingenol angelate compound is in crystalline form.

* * * * *

UNITED STATES PATENT AND TRADEMARK OFFICE
CERTIFICATE OF CORRECTION

PATENT NO. : 9,895,334 B2  
APPLICATION NO. : 12/598102  
DATED : February 20, 2018  
INVENTOR(S) : Steven Martin Ogbourne et al.

It is certified that error appears in the above-identified patent and that said Letters Patent is hereby corrected as shown below:

In the Claims

In Claim 30, Column 27, Lines 33-34:
"wherein the si g ingenol" should read -- wherein the single ingenol --.

Signed and Sealed this
Twenty-eighth Day of August, 2018

Andrei Iancu
*Director of the United States Patent and Trademark Office*